United States Patent [19]
Bowe et al.

[11] Patent Number: 6,096,036
[45] Date of Patent: Aug. 1, 2000

[54] STEERABLE CATHETER WITH PREFORMED DISTAL SHAPE AND METHOD FOR USE

[75] Inventors: Wade A. Bowe, Temecula; Robert C. Hayzelden, Canyon Lake; John A. Simpson, Carlsbad, all of Calif.

[73] Assignee: Cardiac Pacemakers, Inc., St. Paul, Minn.

[21] Appl. No.: 09/072,962

[22] Filed: May 5, 1998

[51] Int. Cl.[7] .................................................. A61B 5/042
[52] U.S. Cl. ............................ 606/41; 607/122; 600/372; 600/374; 600/585; 604/264; 604/527; 604/528; 604/532
[58] Field of Search ..................................... 607/117, 122; 600/372, 373, 374, 585; 604/204, 523, 525, 528, 530

[56] References Cited

U.S. PATENT DOCUMENTS

| | | | |
|---|---|---|---|
| 4,917,102 | 4/1990 | Miller et al. | 128/772 |
| 4,960,134 | 10/1990 | Webster, Jr. | 128/786 |
| 5,171,232 | 12/1992 | Castillo et al. | 604/280 |

(List continued on next page.)

FOREIGN PATENT DOCUMENTS

| | | | |
|---|---|---|---|
| 0790066A2 | 2/1992 | European Pat. Off. . | |
| 0745406A2 | 12/1996 | European Pat. Off. | A61M 25/00 |
| 0778043A1 | 12/1996 | European Pat. Off. . | |
| WO94/21168 | 9/1994 | WIPO . | |
| WO 96/38410 | 12/1996 | WIPO . | |
| WO 97/09043 | 3/1997 | WIPO . | |
| WO926836 | 7/1997 | WIPO . | |

OTHER PUBLICATIONS

International Search Report re EP Application No. 97 94 8121, mailed Nov. 5, 1999.

Abstract; Bodaness, R.S. et al, "The Two–Photon Induced Fluorescence of the Tumor Localizing Photosensitizer Hematoporphyrin Derivative via 1064 nm Photons from a 20 ns Q–Switched Nd–Yag Laser," *Biochemical and Biophysical Research Communications*, vol. 62, No. 1, pp. 346–351, Jan. 16, 1985.

Abstract: Lenz, P. "In Vivo Excitation of Photosensitizers by Infrared Light," *Photochemistry and Photobiology*, vol. 62, No. 2, pp. 333–338, Aug. 1995.

Abstract: Fisher, W.G. et al, "Simultaneous Two–Photon Activation of Type–I Photodynamic Therapy Agents," *Photochemistry and Photobiology*, vol. 66, No. 2, pp. 141–155, Aug. 1997.

Abstract: Bhawalkar, J.D. et al. "Two–Photon Photodynamic Therapy," *Journal of Clinical Laser Medicine and Sugery*, vol. 15, No. 5, pp. 201–204, 1997.

*Primary Examiner*—Linda C. M. Dvorak
*Assistant Examiner*—David M. Ruddy
*Attorney, Agent, or Firm*—Fulwider Patton Lee & Utecht, LLP

[57] ABSTRACT

A catheter has a stylet formed of a shape-retentive and resilient material having a preformed curved shape at its distal end resulting in the catheter sheath having the preformed curved shape. The catheter sheath has a plurality of electrodes at its distal end for contacting selected biological tissue for imparting ablation energy thereto. The catheter sheath also has an axially mounted tendon for causing deflection of the distal end. The stylet material permits straightening the catheter sheath during insertion into the patient and advancing the electrodes to the target tissue. Upon removal of the straightening forces, such as by entry into a chamber of the heart, the stylet material resumes its preformed curved distal shape thereby forcing the catheter distal end with the electrodes into the same preformed curved shape. The operator may place the curved distal end into contact with the target tissue and axially move the tendon as desired to gain greater control over the bend in the distal end of the catheter sheath to adjust the radius of curvature of the distal end to obtain greater contact of the electrodes with the heart tissue. Preferably, the stylet is formed of nitinol.

15 Claims, 4 Drawing Sheets

U.S. PATENT DOCUMENTS

| | | | |
|---|---|---|---|
| 5,363,861 | 11/1994 | Edwards et al. | 128/772 |
| 5,476,495 | 12/1995 | Kordis et al. | 607/122 |
| 5,487,385 | 1/1996 | Avitall | 128/642 |
| 5,487,757 | 1/1996 | Truckai et al. | 128/642 |
| 5,489,270 | 2/1996 | van Erp | 604/95 |
| 5,531,685 | 7/1996 | Hemmer et al. | 604/95 |
| 5,582,609 | 12/1996 | Swanson et al. | 606/39 |
| 5,617,854 | 4/1997 | Munsif | 128/642 |
| 5,626,136 | 5/1997 | Webster, Jr. | 128/642 |
| 5,637,090 | 6/1997 | McGee et al. | 604/95 |
| 5,715,817 | 2/1998 | Stevens-Wright et al. | 128/642 |
| 5,823,955 | 10/1998 | Kuck et al. | 600/374 |
| 5,860,920 | 1/1999 | McGee et al. | 600/374 |
| 5,882,346 | 3/1999 | Pomeranz et al. | 607/122- |

STEERABLE CATHETER WITH PREFORMED DISTAL SHAPE AND METHOD FOR USE

BACKGROUND OF THE INVENTION

The invention relates generally to an electrophysiological ("EP") apparatus and method for providing energy to biological tissue, and more particularly, to a steerable catheter with a preformed distal shape for positioning the catheter to a desired location in a patient.

The heart beat in a healthy human is controlled by the sinoatrial node ("S-node") located in the wall of the right atrium. The S-A node generates electrical signal potentials that are transmitted through pathways of conductive heart tissue in the atrium to the atrioventricular node ("A-V node") which in turn transmits the electrical signals throughout the ventricle by means of the His and Purkinje conductive tissues. Improper growth of, or damage to, the conductive tissue in the heart can interfere with the passage of regular electrical signals from the S-A and A-V nodes. Electrical signal irregularities resulting from such interference can disturb the normal rhythm of the heart and cause an abnormal rhythmic condition referred to as "cardiac arrhythmia."

While there are different treatments for cardiac arrhythmia, including the application of anti-arrhythmia drugs, in many cases ablation of the damaged tissue can restore the correct operation of the heart. Such ablation can be performed by percutaneous ablation, a procedure in which a catheter is percutaneously introduced into the patient and directed through an artery to the atrium or ventricle of the heart to perform single or multiple diagnostic, therapeutic, and/or surgical procedures. In such case, an ablation procedure is used to destroy the tissue causing the arrhythmia in an attempt to remove the electrical signal irregularities or create a conductive tissue block to restore normal heart beat or at least an improved heart beat. Successful ablation of the conductive tissue at the arrhythmia initiation site usually terminates the arrhythmia or at least moderates the heart rhythm to acceptable levels. A widely accepted treatment for arrhythmia involves the application of RF energy to the conductive tissue.

In the case of atrial fibrillation ("AF"), a procedure published by Cox et al. and known as the "Maze procedure" involves continuous atrial incisions to prevent atrial reentry and to allow sinus impulses to activate the entire myocardium. While this procedure has been found to be successful, it involves an intensely invasive approach. It is more desirable to accomplish the same result as the Maze procedure by use of a less invasive approach, such as through the use of an appropriate EP catheter system.

There are two general methods of applying RF energy to cardiac tissue, unipolar and bipolar. In the unipolar method a large surface area electrode; e.g., a backplate, is placed on the chest, back or other external location of the patient to serve as a return. The backplate completes an electrical circuit with one or more electrodes that are introduced into the heart, usually via a catheter, and placed in intimate contact with the aberrant conductive tissue. In the bipolar method, electrodes introduced into the heart have different potentials and complete an electrical circuit between themselves. In the bipolar method, the flux traveling between the two electrodes of the catheter enters the tissue to cause ablation.

During ablation, the electrodes are placed in intimate contact with the target endocardial tissue. RF energy is applied to the electrodes to raise the temperature of the target tissue to a non-viable state. In general, the temperature boundary between viable and non-viable tissue is approximately 48° Centigrade. Tissue heated to a temperature above 48° C. becomes non-viable and defines the ablation volume. The objective is to elevate the tissue temperature, which is generally at 37° C., fairly uniformly to an ablation temperature above 48° C., while keeping both the temperature at the tissue surface and the temperature of the electrode below 100° C.

Failure to bring or maintain the electrodes in contact with the target tissue may result in the RF energy not reaching the tissue in sufficient quantities to effect ablation. Only limited electromagnetic flux in a bipolar approach may reach the tissue when the electrode is non-contacting. In a unipolar approach, the RF energy may spread out too much from the non-contacting electrode before reaching the tissue so that a larger surface area is impacted by the flux resulting in each unit volume of tissue receiving that much less energy. In both cases, the process of raising the tissue temperature to the ablation point may require a much greater time period, if it can be performed at all. Where the electrodes have temperature sensors and those sensors are not in contact with the tissue, they may not sense the actual temperature of the tissue as fluids flowing around the non-contacting electrode may lower the temperature of the electrode and the temperature sensed by the sensors.

In some procedures, such as where a longer atrial lesion is required, the lesion produced by a single electrode in a unipolar arrangement is not sufficient. To this end ablation catheters have been designed. In one catheter an electrode device having four peripheral electrodes which extend from a retracted mode is used. See U.S. Pat. No. 5,500,011 to Desai. When extended, i. e., fanned out, the four peripheral electrodes and the central electrode form an electrode array that covers a larger surface area of the tissue than a single electrode. However, there remain some difficulties in manipulating such a device so that when expanded, all electrodes are in contact with the endocardium. An "end on" approach is required such that the end of the catheter, on which all five electrodes are mounted, is in intimate contact with the target tissue.

The effectiveness of the above-described technique is further limited by the mechanical configuration of the electrode device. When used for ablation, an electrode device is typically part of a catheter system. Accordingly, it is desirable to minimize the diameter of the electrode device during introduction to and withdrawal from the patient to allow for its use within a catheter and to lessen trauma to the patient. However, it is desirable to obtain a relatively large expandable size to obtain a larger ablation size. Therefore, electrode devices having peripheral expandable electrodes must be configured so that the peripheral electrodes are expandable to a large size yet are retractable to as small a size as practical. Such requirements pose design and manufacturing difficulties and an electrode device configured as such is susceptible to malfunction in that the peripheral electrodes may be damaged or break off as they are extended from a retracted mode or vice versa. Further considerations are the undesirable complexity and increased manufacturing cost associated with an expandable catheter.

In other techniques, used in the treatment of atrial fibrillation, a plurality of spaced apart electrodes are located at the distal end of the catheter in a linear array. RF energy is applied to the electrodes to produce a longer lesion. With such a linear array, intimate contact between each electrode and the target endocardial tissue is more difficult to maintain in the heart due to the irregular heart surface shape and the constant movement of the heart. The lesion produced may have discontinuities unless steps are taken to maintain contact. These lesions may not be sufficient to stop the irregular signal pathways and arrhythmia may reoccur. In an attempt to ensure intimate contact between the electrode and the target tissue the distal end of the catheter may have a preformed shape. For example, see U.S. Pat. No. 5,617,854 to Munsif, in which the catheter is made of a shaped-memory material, e. g. nitinol, and formed in a specific shape. During use, the catheter is deformed and introduced through an introducer sheath to the heart where ablation is to occur. Once in position, the catheter is reformed into its specific shape when heated to body temperature or when a current is passed through the shaped-memory material. If the shaped memory of the catheter matches the curvature of the biological cavity, there is more intimate contact between the electrode and the tissue and a more continuous lesion is formed. However, this is somewhat unlikely because the heart surface is irregular. If a given shaped catheter does not conform to the shape of the biological site to be ablated a different catheter having a different preformed shape must be used. Requiring a collection of preformed-shaped catheters, as such, is economically inefficient.

Hence, those skilled in the art have recognized a need for a structurally stable minimally invasive ablation apparatus that is capable of controlling the flow of current through a biological site so that lesions with controllable surface and depth characteristics may be produced and the ablation volume thereby controlled. Additionally, a need has been recognized for providing a catheter carrying a plurality of electrodes in its distal end region which is capable of conforming to various curvatures of the biological site so that intimate contact may be maintained between the electrodes and the site. The invention fulfills these needs and others.

SUMMARY OF THE INVENTION

Briefly, and in general terms, the invention is directed to an apparatus and a method for use in applying energy to a biological site using a catheter carrying a plurality of electrodes in its distal end region which is capable of conforming to various curvatures of the biological site so that intimate contact may be maintained between the electrodes and the site.

In a first aspect, the invention is a catheter for positioning at least one electrode at a selected biological site and comprises a sheath having a distal end carrying the at least one electrode, a stylet having a preformed shape with at least one bend, the stylet housed within the sheath and formed of a shape-retentive and resilient material such that the stylet changes shape upon the application of force and upon the removal of force, returns to the preformed shape. The stylet is disposed in the sheath such that the bend is located in the distal end of the sheath and causes the sheath to assume the preformed shape. The catheter also includes a tendon housed within the sheath and attached to the distal end of the sheath such that axial displacement of the tendon causes deflection of the distal end of the sheath.

In more detailed aspects, the preformed distal shape has a radius of curvature for conforming the distal end of the sheath to the selected biological site. Additionally, the tendon is disposed in the sheath such that pulling the tendon in the proximal direction decreases the radius of curvature of the distal end of the sheath and movement of the tendon in the distal direction increases the radius of curvature of the distal end of the sheath. In a further aspect, the stylet is formed of nitinol.

In a further more detailed aspect, the stylet is attached to the distal end of the sheath. In another detailed aspect, a tip component is positioned at the distal tip of the sheath wherein the stylet and tendon are attached to the tip component. A steering member is positioned at the proximal end of the sheath wherein the tendon is attached to the steering member for moving the tendon in an axial direction.

In another aspect, a handle is disposed at the proximal end of the sheath and connected thereto such that rotation of the handle results in rotation of the sheath and stylet. In more detailed aspects, there exist a plurality of band electrodes spaced apart at the distal end of the sheath. The plurality of band electrodes are positioned on the sheath in the region of the preformed distal shape. In yet a further detailed aspect, the distal end of the stylet has a plurality of bends.

In second aspect, the invention is an ablation system for use in applying energy to heart tissue. The system comprises a catheter sheath having a distal end region and a lumen, a plurality of electrodes located at the distal end region of the catheter sheath, a stylet having a distal end with a preformed shape with at least one bend. The stylet is housed within the catheter sheath and formed of a shape-retentive and resilient material such that the stylet changes shape upon the application of force and upon the removal of the force, returns to the preformed shape. The stylet is disposed in the catheter sheath such that the bend is located in the distal end region of the sheath and causes the sheath to assume the preformed shape. The ablation system also includes a tendon housed within the catheter sheath and attached to the distal end of the sheath such that axial displacement of the tendon causes deflection of the distal end of the sheath, a handle attached to the proximal end of the catheter sheath and the stylet such that rotation of the handle causes rotation in the catheter sheath and the stylet, and a control member disposed at the handle and connected to the tendon such that a predetermined movement of the control member causes axial movement of the tendon to control deflection of the distal end region of the catheter sheath.

In a further detailed aspect of the above, the plurality of electrodes are spaced apart on the distal end region of the catheter to form a linear array.

In a third aspect, the invention is a method for applying energy to heart tissue. The method comprises the steps of inserting and advancing into the patient a catheter sheath having a stylet formed of a shape-retentive and resilient material such that the stylet changes shape upon the application of force and upon the removal of the force, returns to a preformed shape. The stylet is mounted in the catheter sheath such that the sheath has the preformed shape at its distal end, the shape having a curvature generally conforming to the curvature of selected heart tissue, the catheter sheath also having a plurality of electrodes, wherein the distal end shape is altered from its preformed shape while being inserted and advanced. Further included are the steps of advancing the catheter sheath into the heart chamber in which the selected heart tissue is located thereby permitting the catheter sheath distal end to resume its preformed curved distal shape, advancing the curved distal end of the catheter sheath into contact with the selected heart tissue, and adjusting the radius of curvature of the distal end region of the catheter such that a plurality of the electrodes contact the selected heart tissue.

In more detailed aspects of the method, the step of advancing the catheter into the selected heart chamber comprises the steps of inserting an introducer sheath into the selected heart chamber, guiding the catheter through the introducer sheath, and extending the catheter beyond the distal end of the introducer sheath thereby allowing the distal end region of the catheter to resume its preformed shape. Additionally, in another aspect, the step of adjusting the radius of curvature of the distal end region of the catheter comprises the step of axially moving a tendon attached to the distal end region of the catheter sheath to deflect the distal end of the catheter and thereby decrease the curvature of the distal end region.

These and other aspects and advantages of the invention will become apparent from the following detailed description and the accompanying drawings, which illustrate by way of example the features of the invention.

DETAILED DESCRIPTION OF PREFERRED EMBODIMENTS

Figure 1:
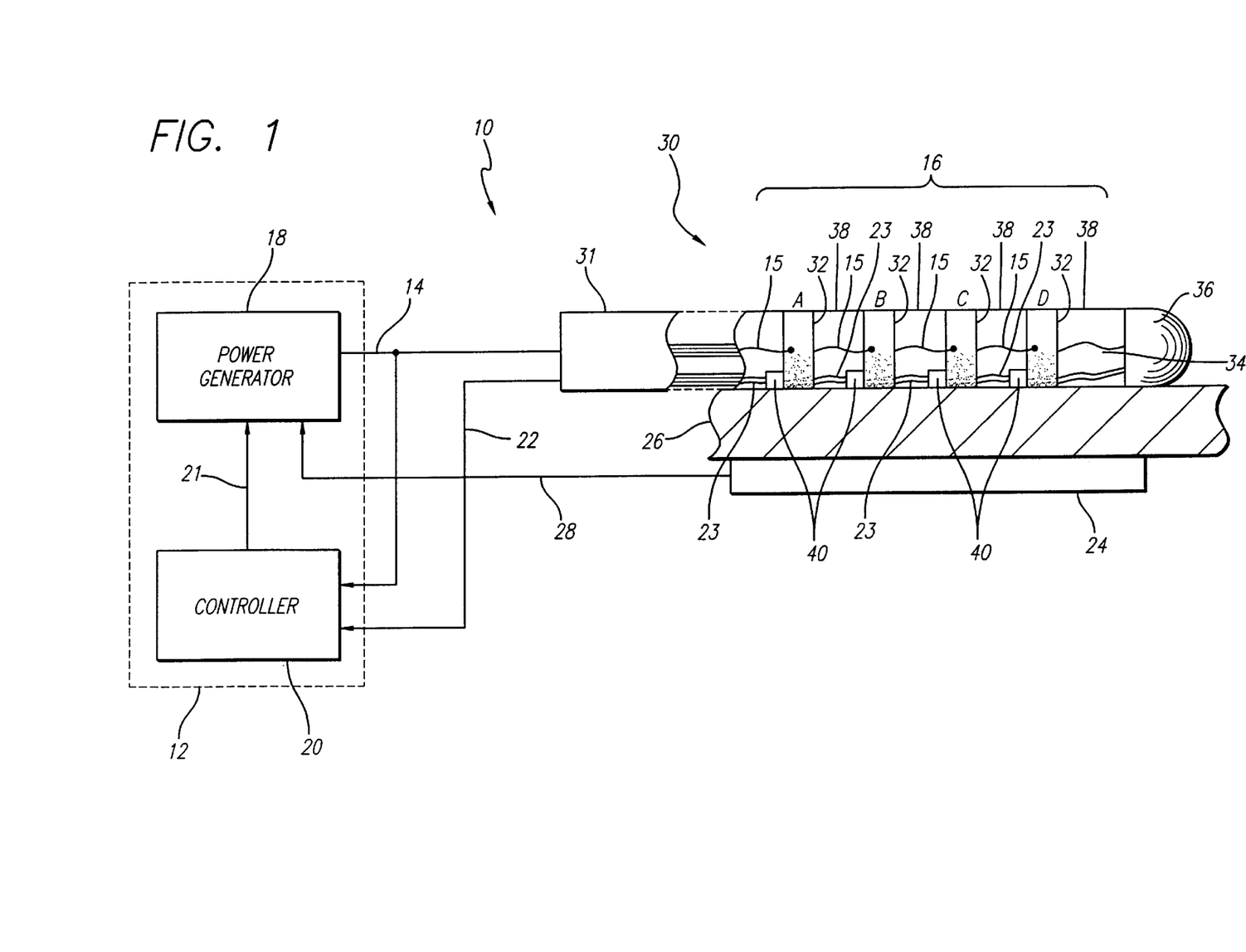
FIG. 1 is a schematic diagram of an ablation apparatus including a power control system, electrode device and backplate.

Turning now to the drawings, in which like reference numerals are used to designate like or corresponding elements among the several figures, in FIG. 1 there is shown an ablation apparatus 10 in accordance with aspects of the present invention. The apparatus 10 includes a power control system 12 that provides power or drive 14 to an electrode device 16. The power control system 12 comprises a power generator 18 that may have any number of output channels through which it provides the power 14. The operation of the power generator 18 is controlled by a controller 20 which outputs control signals 21 to the power generator 18. The controller 20 monitors the power 14 provided by the power generator 18. In addition, the controller 20 also receives temperature signals 22 from the electrode device 16. Based on the power 14 and temperature signals 22 the controller 20 adjusts the operation of the power generator 18. A backplate 24 is located proximal to the biological site 26 opposite the site from the electrode device 16, and is connected by a backplate wire 28 to the power generator 18. The backplate 24 is set at the reference level to the power provided to the electrodes, as discussed in detail below.

In a manual arrangement, the temperature sensed and/or the determined impedance may be displayed to an operator. The operator in response may then manually control the duty cycle or other power parameters such as by rotating a knob mounted on a front panel of an instrument. In the case of a multiple channel instrument and catheter, as discussed below, multiple knobs may be provided in this manual arrangement for control over each channel.

The electrode device 16 is typically part of a steerable EP catheter 30 capable of being percutaneously introduced into a biological site 26, e. g., the atrium or ventricle of the heart. The electrode device 16 is shown in schematic form with the components drawn to more clearly illustrate the relationship between the components and the relationship between the components and the power control system 12. In this embodiment, the catheter 30 comprises a distal segment 34 and a handle 31 located outside the patient. A preferred embodiment of the electrode device 16 includes twelve band electrodes 32 arranged in a substantially linear array along the distal segment 34 of the catheter 30. The electrode device 16 may include a tip electrode 36. (For clarity of illustration, only four band electrodes 32 are shown in the figures although as stated, a preferred embodiment may include many more.) The band electrodes 32 are arranged so that there is space 38 between adjacent electrodes. In one configuration of the electrode device 16, the width of the band electrodes 32 is 3 mm and the space 38 between the electrodes is 4 mm. The total length of the electrode device 16, as such, is approximately 8 cm.

The arrangement of the band electrodes 32 is not limited to a linear array and may take the form of other patterns. A substantially linear array is preferred for certain therapeutic procedures, such as treatment of atrial fibrillation, in which linear lesions of typically 4 to 8 cm in length are desired. A linear array is more easily carried by the catheter 30 and also lessens the size of the catheter.

The band electrodes 32 are formed of a material having a significantly higher thermal conductivity than that of the biological tissue 26. Possible materials include silver, copper, gold, chromium, aluminum, molybdenum, tungsten, nickel, platinum, and platinum/10% iridium. Because of the difference in thermal conductivity between the electrodes 32 and the tissue 26, the electrodes 32 cool off more rapidly in the flowing fluids at the biological site. The power supplied to the electrodes 32 may be adjusted during ablation to allow for the cooling of the electrodes while at the same time allowing for the temperature of the tissue to build up so that ablation results. The electrodes 32 are sized so that the surface area available for contact with fluid in the heart, e. g., blood, is sufficient to allow for efficient heat dissipation from the electrodes to the surrounding blood. In a preferred embodiment, the electrodes 32 are 7 French (2.3 mm in diameter) with a length of 3 mm.

The thickness of the band electrodes 32 also affects the ability of the electrode to draw thermal energy away from the tissue it contacts. In the present embodiment, the electrodes 32 are kept substantially thin so that the electrodes effectively draw energy away from the tissue without having to unduly increase the outer diameter of the electrode. In a preferred embodiment of the invention, the thickness of the band electrodes is 0.05 to 0.13 mm (0.002 to 0.005 inches).

Associated with the electrode device 16 are temperature sensors 40 for monitoring the temperature of the electrode device 16 at various points along its length. In one embodiment, each band electrode 32 has a temperature sensor 40 mounted to it. Each temperature sensor 40 provides a temperature signal 22 to the controller 20 which is indicative of the temperature of the respective band electrode 32 at that sensor. In another embodiment of the electrode device 16 a temperature sensor 40 is mounted on every other band electrode 32. Thus for a catheter having twelve electrodes, there are temperature sensors on six electrodes. In yet another embodiment of the electrode device 16 every other electrode has two temperature sensors 40. In FIG. 1, which shows an embodiment having one temperature sensor for each electrode, there is shown a single power lead 15 for each electrode 32 to provide power to each electrode for ablation purposes and two temperature leads 23 for each temperature sensor 40.

Figures 2, 3:
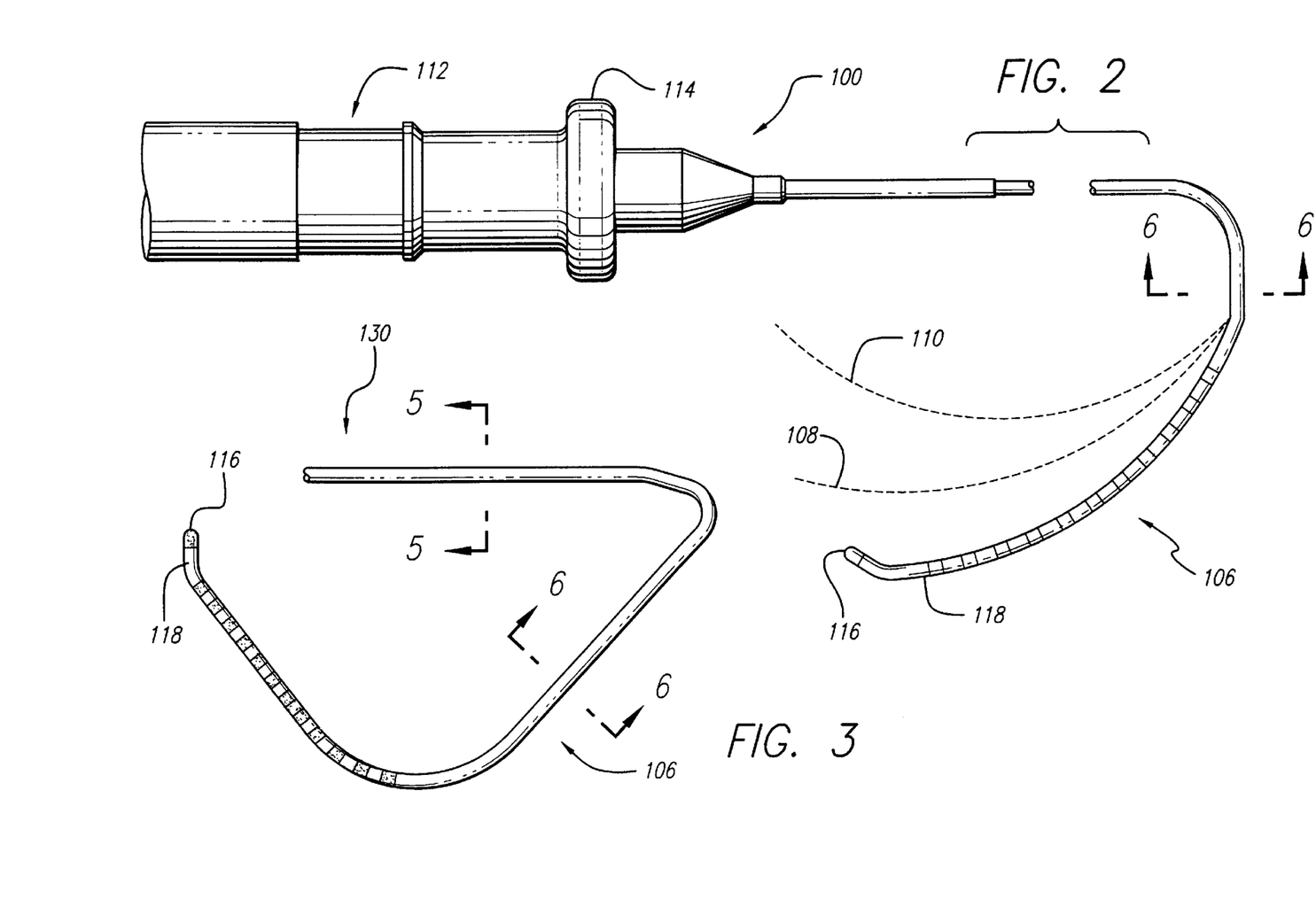
FIG. 2 is a diagram of a catheter system including a handle, steering member, and a catheter having a preformed distal end region with a first shape.
FIG. 3 is an alternate preformed distal end region of FIG. 2 having a second shape.

In order to ensure a long, continuous lesion the catheter employs a steering tendon and a stylet having a preformed distal shape. As shown in FIG. 2, the catheter 100 includes a distal end region 106 having a preformed distal shape. This distal shape may have any form which generally conforms to the contour of the biological cavity containing the tissue to be ablated. The distal end region 106 of FIG. 2 has been simplified for clarity to depict varying degrees of curvature 108 and 110 obtainable by use of the preformed shape and the steering tendon, as explained below. The distal shape of FIG. 3 is conducive to the treatment of atrial fibrillation in that its shape allows for the distal end region 106 to be easily inserted into the atrium of the heart. The shape, in combination with a steering tendon, also provides a distal end region having a contour which may be adjusted to conform to the contour of the atrium.

The catheter 100 also includes a handle 112 and a steering member 114. A tip component 116 is mounted to a sheath 118 at the very distal tip of the sheath. A shaped-memory wire, i. e., stylet, 104 (FIG. 4) is located in the distal end region 106 and preferably runs the entire length of the sheath 118. The stylet 104 is attached to the tip component 116 at the axis of the tip component, and is anchored to a fixed position within the handle 112. The shaped memory wire 104 is formed of an alloy which exhibits a martensitic phase transformation. Such alloys include those which exhibit non-linear superelasticity (typically Ni—Ti with Ni at 49–51.5% atomic) and those which exhibit linear superelasticity (typically Ni—Ti in near equi-atomic composition which has been cold worked). Preferably, the preformed shaped wire 104 is formed of nitinol wire having a diameter in the range of 0.026 to 0.030 mm and a nitinol composition of 49–51.5% Ni. The shape of the distal end region 106 is created by restraining the nitinol wire in the desired shape and heating the wire to approximately 500° C. for about 10 minutes. The nitinol is then allowed to cool. Upon cooling, the wire 104 retains the preformed distal shape.

Stress may be applied to the wire to change its shape. For example, the wire 104 may be straightened to negotiate an introducer or various blood vessels on its way to the right or left atrium of the heart. Upon removal of the straightening forces, such as when the distal end enters the left atrium of the heart, the stylet accurately resumes its preformed shape causing the distal end of the catheter sheath surrounding it to likewise take the same shape. Because of the superelasticity of the nitinol, once the stress is removed the wire returns to its original shape. This is distinct from other shape-memory materials which are temperature actuated.

Figures 4, 5, 6:
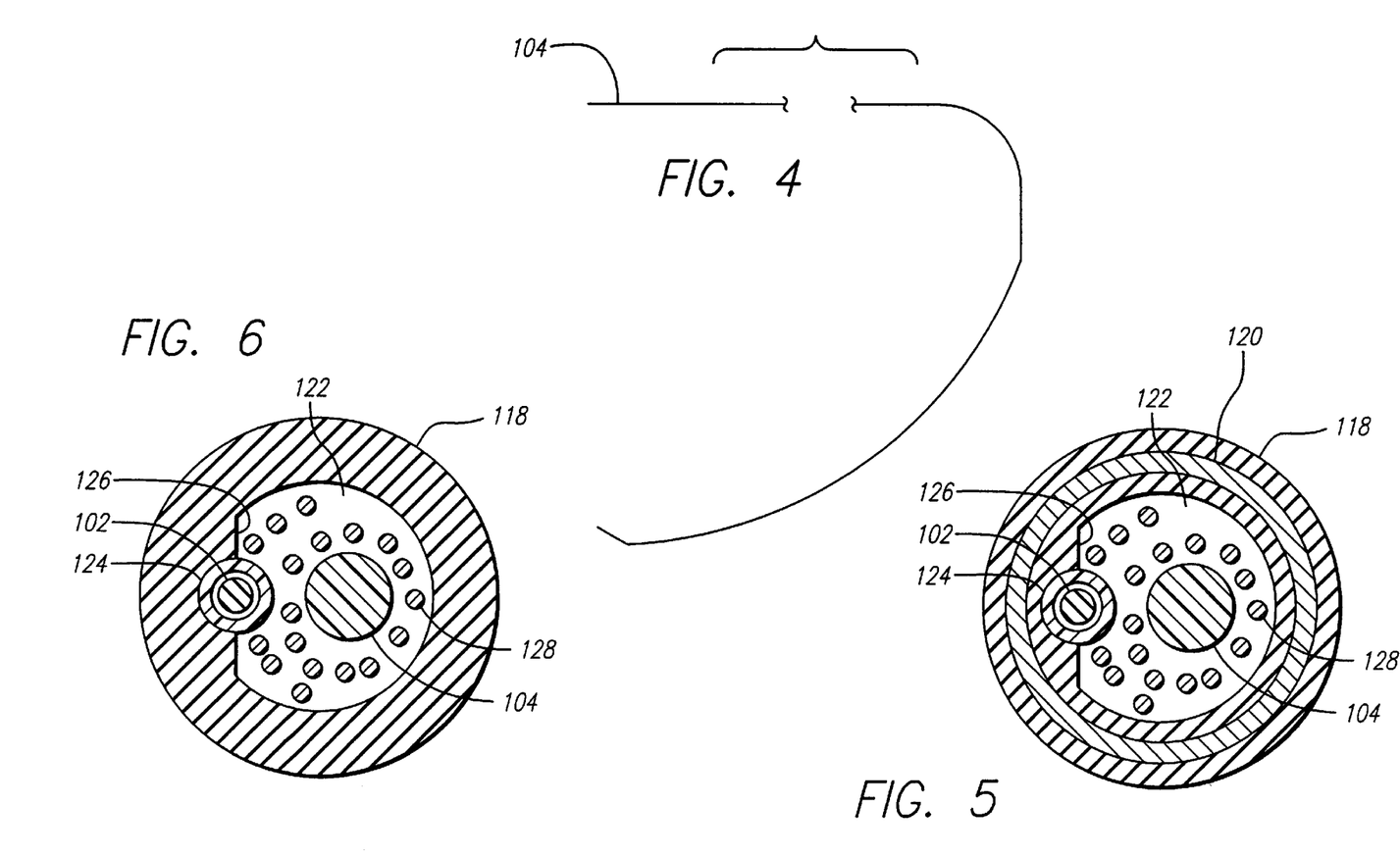
FIG. 4 is a preformed stylet for shaping the distal end region of the catheter of FIG. 2.
FIG. 5 is a sectional view of the proximal region of the catheter of FIG. 3 taken along the line 5—5 depicting the catheter sheath with braid, stylet, steering tendon and leads.
FIG. 6 is a sectional view of the distal end region of the catheter of FIGS. 2 and 3 taken along the line 6—6 depicting the catheter sheath, stylet, steering tendon and leads.

Referring now to FIG. 5, the stylet 104 is housed inside a composite sheath 118 constructed of different durometers of Pebax and braided stainless steel ribbon in order to tailor the torsinal and bending stiffness in various locations along the length of the catheter. In the region 130 proximal from the distal end region 106, as shown in FIG. 3 the sheath 118 is formed of high durometer Pebax outer jacket having an outside diameter of 2.39 mm (0.094 inches) (7 French) and an inside diameter of 1.58 mm (0.062 inches). Imbedded within the sheath 118 are two layers of braid, 0.001×0.006 stainless steel ribbon 120. The inner lumen 122 has a hollow PTFE tendon sheath 124 bonded to one side 126. The tendon sheath 124 has an outside diameter of approximately 0.457 mm (0.018 inches). The remaining portion of the tendon sheath 124 is exposed in the inner lumen 122. The steering tendon 102 is housed within the tendon sheath 124 and is formed of a stainless steel wire having a diameter of approximately 0.23 mm (0.009 inches). At its distal end, the steering tendon 102 is attached to the tip component 116 at a point parallel to the axis of the tip component. In the alternative, the steering tendon 102 may be anchored at a point proximal the tip component 116. At its proximal end, the tendon 102 is linked to the steering member 114 (FIG. 2) which translates axially along the length of the handle 112. Also housed within the inner lumen 122 are the leads 128. Eighteen are depicted in FIG. 4, however, more or fewer may be included depending on the number of electrodes 32 and the configuration of the temperature sensors.

In the distal end region 106 (FIGS. 2 and 3), as shown in cross section in FIG. 6, the construction of the sheath 118 is generally the same as that of the proximal region 130 except the outer jacket does not include a stainless steel braid 120. By not including the braid 120, the distal end region 106 is more flexible than the proximal region 130. Accordingly, the distal end region 106 is more easily bent for conformance with the biological site. Housed within the sheath 118 and offset from the axis of the sheath is the steering tendon 102.

Figure 7:
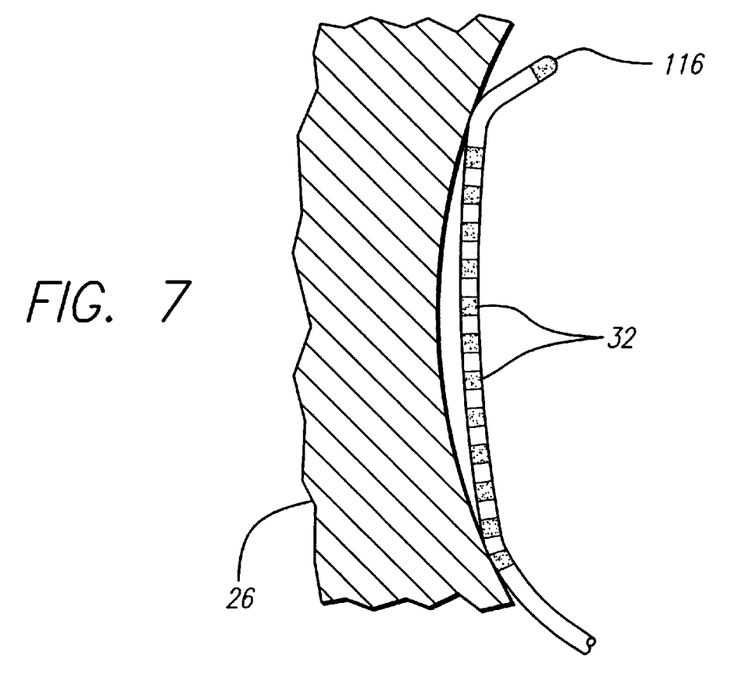
FIG. 7 is a representation of the distal end region of the catheter of FIG. 3 proximal biological tissue with the electrodes not in intimate contact with the tissue.

In operation, the catheter 100 is inserted into the biological cavity containing the tissue to be ablated. In the case of the left atrium where a transseptal approach is used, the catheter may be inserted using an introducer sheath (not shown). The introducer sheath is positioned within the cavity and the catheter 100 is inserted into the introducer sheath. Because of the flexibility of the nitinol stylet 104, the distal end region 106 of the catheter conforms to the shape of the introducer sheath and follows the tortuous path of the introducer sheath. Once the distal end region 106 of the catheter enters the biological cavity the catheter is either extended beyond the distal tip of the introducer sheath or the introducer sheath is retracted. In either case, the distal end region 106 of the catheter is no longer constrained by the introducer sheath and returns to its original preformed distal shape. Once the preformed distal shape is resumed, the distal end region 106 has a shape more closely following that of the heart. However it may not conform to the shape of the biological site 126 as closely as desired. This situation is shown in FIG. 7. Accordingly, some or all of the electrodes 32 may not be in intimate contact with the tissue 26 to be ablated. If the electrodes 32 are not in the desired contact with the tissue 26, the radius of curvature of the distal end region may be adjusted using the steering tendon such that more of the electrodes contact the biological tissue 26. The dashed lines 108 and 110 of FIG. 2 are examples of how the degree of curvature of the distal end region 106 may be adjusted by use of the steering tendon. This adjustment is performed by axially displacing the steering member 114 in the proximal direction. In doing so, the steering tendon 102 attached to the tip component 116 experiences tension and causes the sheath 118 to compress on the side in which the steering tendon is positioned and to stretch on the opposite side. This causes the radius of curvature of the distal end region to decrease as shown in FIG. 2. In addition, to further ensure intimate contact between the electrodes 32 and the tissue 26, the handle 112 may be rotated. Because of the attachment of the sheath 118 to the handle 112 and the construction of the catheter, as previously described in relation to FIGS. 5 and 6, this rotational force at the handle causes the catheter to experience a torquing effect along its length, which may aid in positioning the electrodes against the tissue.

Figure 8:
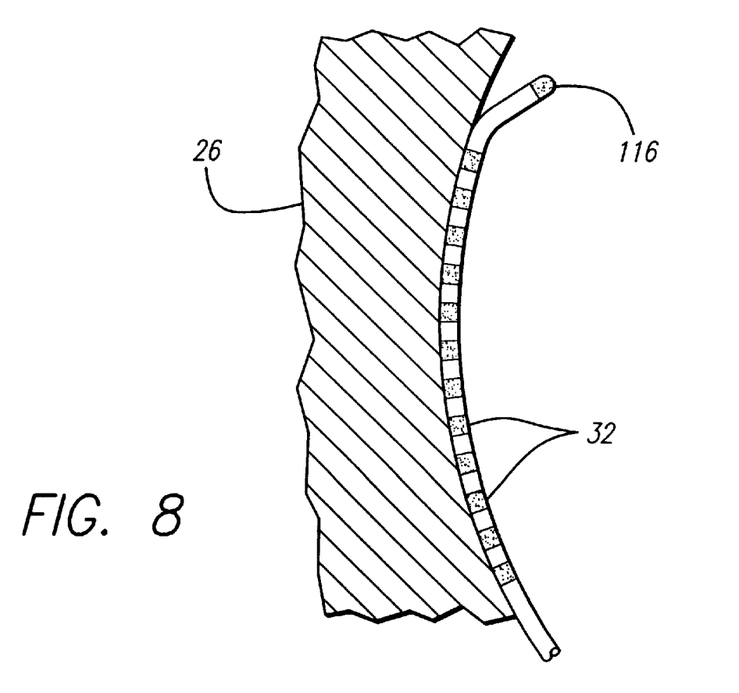
FIG. 8 is a representation of the distal end region of the catheter of FIG. 3 proximal biological tissue with the electrodes in intimate contact with the tissue.

Once the distal end region 106 is properly positioned and the electrodes 32 are in intimate contact with the tissue, as shown in FIG. 8, RF energy is applied to the electrodes to ablate the tissue. After applying energy to a first portion of tissue 26 located within the selected biological cavity, the distal end region 106 of the catheter may be repositioned proximal another region of tissue and the curvature of the distal end region adjusted so that the electrode 32 contact the tissue. Thus, the catheter provides for ready adjustment of the electrode carrying region 106 such that a plurality of electrodes aligned in a substantially linear array may be placed in intimate contact with tissue 26 to be ablated. Because of the length of the linear electrode array, the device shown in the drawings and described above is particularly suited for performing the Maze procedure in a minimally invasive way.

While certain shapes of the distal end of the catheter are shown in FIGS. 2 and 3, other shapes may be used. The invention is not confined to the shapes shown in these figures. Additionally, the steering tendon may be used by the operator to steer or assist in advancing the catheter distal end through the blood vessels of the patient to the desired target tissue.

Thus there has been shown and described a new and useful catheter system having both a preformed distal end and a steering mechanism which greatly increase the chances that a successful ablation can be obtained in a single procedure.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A catheter for positioning at least one electrode at a selected biological site, said catheter comprising:
   a sheath having a distal end carrying the at least one electrode;
   a stylet disposed within the sheath and attached to the distal end of the sheath, the stylet having a distal end region having a preformed shape with a radius of curvature, the stylet formed of a shape-retentive and resilient material such that the stylet distal end region changes shape upon the application of force and upon the removal of force, returns to the preformed shape, the stylet disposed in the sheath such that the stylet distal end region is located in the distal end region of the sheath and causes the sheath to assume the preformed shape; and
   a tendon housed within the sheath and attached to the distal end of the sheath such that axial displacement of the tendon changes the radius of curvature of the stylet distal end region and the sheath distal end region.

2. The catheter of claim 1 wherein the radius of curvature conforms the sheath distal end region to the selected biological site.

3. The catheter of claim 1 wherein the tendon is disposed in the sheath such that pulling the tendon in the proximal direction decreases the radius of curvature of the stylet distal end region and the sheath distal end region and subsequent movement of the tendon in the distal direction allows an increase in the radius of curvature of the stylet distal end region and the sheath distal end region.

4. The catheter of claim 1 wherein the stylet is formed of nitinol.

5. The catheter of claim 1 further comprising a tip component positioned at the distal tip of the sheath wherein the stylet and tendon are attached to the tip component.

6. The catheter of claim 1 further comprising a steering member positioned at the proximal end of the sheath wherein the tendon is attached to the steering member for moving the tendon in an axial direction.

7. The catheter of claim 1 further comprising a handle disposed at the proximal end of the sheath and the stylet and connected thereto such that rotation of the handle results in rotation of the sheath and stylet.

8. The catheter of claim 1 wherein there are a plurality of band electrodes spaced apart at the distal end of the sheath.

9. The catheter of claim 8 wherein the plurality of band electrodes are positioned on the sheath in the region of the preformed shape.

10. An ablation system for use in applying energy to heart tissue, said system comprising:
    a catheter sheath having a distal end region and a lumen;
    a plurality of electrodes located at the distal end region of the catheter sheath;
    a stylet disposed within the sheath and attached to the distal end of the catheter sheath, the stylet having a distal end region with a preformed shape with a radius of curvature, the stylet formed of a shape-retentive and resilient material such that the stylet distal end region changes shape upon the application of force and upon the removal of the force, returns to the preformed shape, the stylet disposed in the catheter sheath such that the stylet distal end region is located in the distal end region of the sheath and causes the sheath to assume the preformed shape;
    a tendon housed within the catheter sheath and attached to the distal end of the sheath such that axial displacement of the tendon changes the radius of curvature of the stylet distal end region and the sheath distal end region;
    a handle attached to the proximal end of the catheter sheath and the stylet such that rotation of the handle causes rotation in the catheter sheath and the stylet; and
    a control member disposed at the handle and connected to the tendon such that a predetermined movement of the control member causes axial movement of the tendon to control changes in the radius of curvature of the stylet distal end region and the sheath distal end region.

11. The ablation system of claim 10 wherein the plurality of electrodes are spaced apart on the distal end region of the catheter sheath to form a linear array.

12. The ablation system of claim 10 wherein the stylet is formed of nitinol.

13. The ablation system of claim 10 wherein the preformed shape has a degree of curvature generally the same as that of the selected biological site.

14. The ablation system of claim 10 wherein the catheter sheath has a longitudinal axis and the tendon is attached to the distal end at a point off the axis.

15. The catheter of claim 10 wherein the tendon is disposed in the catheter sheath such that pulling the tendon in the proximal direction decreases the radius of curvature of the stylet distal end region and the sheath distal end region and subsequent movement of the tendon in the distal direction allows an increase in the radius of curvature of the stylet distal end region and the sheath distal end region.

* * * * *

UNITED STATES PATENT AND TRADEMARK OFFICE
CERTIFICATE OF CORRECTION

| | |
|---|---|
| PATENT NO. | : 6,096,036 |
| DATED | : August 1, 2000 |
| INVENTOR(S) | : Wade A. Bowe, Robert C. Hayzelden and John A. Simpson |

It is certified that error appears in the above-identified patent and that said Letters Patent is hereby corrected as shown below:

<u>Title page,</u>
Item [56], References Cited, U.S. PATENT DOCUMENTS, add:
-- 5,383,923    1/1995   Webster --.

Item [56], References Cited, OTHER PUBLICATIONS, and all five publications listed thereafter.

Signed and Sealed this

First Day of October, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,096,036  
DATED : August 1, 2000  
INVENTOR(S) : Wade A. Bowe, Robert C. Hayzelden and John A. Simpson Page 1 of 1

It is certified that error appears in the above-identified patent and that said Letters Patent is hereby corrected as shown below:

<u>Title page,</u>
Item [56], References Cited, U.S. PATENT DOCUMENTS, add:
-- 5,383,923    1/1995   Webster --.
OTHER PUBLICATIONS, delete the following:
"International Search Report re EP Applciation No. 97 94 8121, mailed Nov. 5, 1999.
Abstract; Bodaness, R.S. et al., "the Two-Photon Induced Fluorescence of the Tumor Localizing Photosensitizer Hematoporphyrin Derivative via 1064 nm Photons from a 20 ns Q-Switched Nd-Yag Laser," *Biochemical and Biophysical Research Communications*, vol. 62, No. 1, pp.346-351, Jan. 16. 1985.
Abstract: Lenz, P. "In vivo Excitation of Photosensitizers by Infrared Light," *Photochemistry and Photobiology*, vol. 62, No. 2, pp. 333-338, Aug. 1995.
Abstract: Fisher, W.G. et al, "Simultaneous Two-Photon Activation of Type I Photodynamic Therapy A gents," *Photochemistry and Photobiology*, vol. 66, No. 2, pp. 141-155, Aug. 1997.
Abstract: Bhawalkar, J.D. et al. "Two-Photo Photodynamic Therapy," *Journal of Clinical Laser Medicine and Surgery*, vol. 15, No. 5, pp. 201-204, 1997."

This certificate supersedes Certificate of Correction issued October 1, 2002.

Signed and Sealed this

First Day of June, 2004

JON W. DUDAS
*Acting Director of the United States Patent and Trademark Office*